United States Patent
Sudo et al.

[11] Patent Number: 6,074,373
[45] Date of Patent: Jun. 13, 2000

[54] SYRINGE WITH A LUER-LOK PORTION

[75] Inventors: Morihiro Sudo; Hiroshi Togashi, both of Tokyo, Japan

[73] Assignee: Daikyo Seiko, Ltd., Tokyo, Japan

[21] Appl. No.: 08/958,683

[22] Filed: Oct. 27, 1997

[30] Foreign Application Priority Data

Oct. 28, 1996 [JP] Japan ............................ 8-300841

[51] Int. Cl.[7] .................................................. A61M 5/31
[52] U.S. Cl. ................................. 604/241; 604/535
[58] Field of Search .................................. 604/240, 241, 604/533, 239, 538, 238, 174, 183, 225, 208, 534, 535; 128/912; 285/38, 92

[56] References Cited

U.S. PATENT DOCUMENTS

| | | | |
|---|---|---|---|
| 4,240,422 | 12/1980 | Hazen | 604/241 |
| 4,240,424 | 12/1980 | Akhavi | 604/241 |
| 4,240,428 | 12/1980 | Akhavi | 604/241 |
| 4,441,621 | 4/1984 | Matukura et al. | |
| 4,614,276 | 9/1986 | Ihara et al. | |
| 4,839,429 | 6/1989 | Tajima | |
| 4,883,206 | 11/1989 | Miller | |
| 4,889,429 | 12/1989 | Heinzmann et al. | |
| 4,915,243 | 4/1990 | Tatsumi et al. | |
| 4,997,423 | 3/1991 | Okuda et al. | |
| 5,009,646 | 4/1991 | Sudo et al. | |
| 5,078,941 | 1/1992 | Tatsumi et al. | |
| 5,110,621 | 5/1992 | Sudo et al. | |
| 5,114,749 | 5/1992 | Nishio et al. | |
| 5,208,012 | 5/1993 | Sudo et al. | |
| 5,288,560 | 2/1994 | Sudo et al. | |
| 5,788,670 | 8/1998 | Reinhard et al. | 604/191 X |

*Primary Examiner*—Wynn Wood Coggins
*Assistant Examiner*—A. T. Nguyen
*Attorney, Agent, or Firm*—Oblon, Spivak, McClelland, Maier & Neustadt, P.C.

[57] ABSTRACT

A syringe is provided with a Luer-Lok portion for connecting an extension tube or the like. The Luer-Lok portion is arranged upright on a plane of truncation of a conical-frustum-shaped free end portion of the syringe, and includes an inner cylindrical portion and an outer cylindrical portion surrounding the inner cylindrical portion and having at least two projecting helical ribs formed in parallel with each other on an inner peripheral surface thereof. The extension tube or the like can be connected to the Luer-Lok portion by screwing at least two projecting helical ribs of a cylindrical connector, said at least two projecting helical ribs being formed in parallel with each other on an outer peripheral surface of the cylindrical connector, in corresponding grooves defined between the helical projecting ribs of the outer cylindrical portion. A lower end portion of at least one of the projecting helical ribs of the Luer-Lok portion is formed at a position higher than an upper surface of a bottom wall between both of the cylindrical portions.

14 Claims, 6 Drawing Sheets

SYRINGE WITH A LUER-LOK PORTION

BACKGROUND OF THE INVENTION a) Field of the Invention

This invention relates to a syringe, and more specifically to a syringe with a Luer-Lok portion for connecting an extension tube, a three-way cock or a disposable needle.

b) Description of the Related Art

To mix a solution of a medicine in a transfusion or the like or to inject a high-viscosity medicine or the like into the body, a plastic-made syringe with a Luer-Lok portion for connecting an extension tube, a three-way tube or a disposable needle to a free end portion (air nozzle) of the syringe has been used.

A conventional syringe having a Luer-Lok portion will be described with reference to FIG. 1A through FIG. 4B, in which:

FIG. 1A is a perspective view of the conventional syringe having the Luer-Lok portion;

FIG. 1B is an enlarged perspective view of a conical-frustum-shaped free end portion of the conventional syringe without the Luer-Lok portion;

FIG. 2 is a schematic cross-sectional view of the Luer-Lok portion of the conventional syringe;

FIG. 3 is a perspective view of a cylindrical connector to be screwed in the Luer-Lok portion of the conventional syringe;

FIG. 4A is a simplified cross-sectional view illustrating a normal state of connection between the connector and the Luer-Lok portion; and FIG. 4B is a simplified cross-sectional view depicting a state of connection between the connector and the Luer-Lok portion, in which the connector has been excessively screwed in the Luer-Lok portion.

The Luer-Lok portion, which is designated at numeral 1, has a double-cylinder structure composed of an outer cylindrical portion 2 and an inner cylindrical portion (Luer nozzle) 3, which are both arranged upright on a plane 4 of truncation of the conical-frustum-shaped free end portion of the syringe. The plane 4 of truncation is shown as a top flat surface in FIG. 1B. Between both the cylindrical portions, the cylindrical connector 8 shown in FIG. 3 is screwed in to bring them into engagement with each other. Although not shown in FIG. 3, the cylindrical connector 8 is arranged at an end portion of an extension tube or the like to be connected to the Luer-Lok portion 1.

Reference is next had to FIG. 2. Formed on an inner peripheral surface 2' of the outer cylindrical portion 2 of the Luer-Lok portion 1 are two projecting helical ribs (hereinafter simply referred to as "projecting ribs" for the sake of brevity) a,b, which are parallel to each other and are adapted to connect to the Luer-Lok portion 1 the connector 8 (see FIG. 3) arranged at the end portion of the extension tube or the like. These projecting ribs a,b consist of mutually-parallel two projecting ribs, which helically extend downward at the same pitch on the inner peripheral surface 2' of the outer cylindrical portion 2 with the positions of their upper ends being shifted, for example, over about 180 degrees from each other.

To connect the connector 8 (see FIG. 3) to the Luer-Lok portion 1, the connector 8 for the extension tube or the like, said connector 8 being provided on an outer peripheral surface thereof with mutually-parallel two projecting ribs a',b' formed likewise as the projecting ribs a,b, is screwed in along grooves defined between the projecting ribs a,b so that the connector 8 and the Luer-Lok portion 1 are brought into engagement with each other.

The mutually-parallel two projecting ribs a,b in the Luer-Lok portion 1 have such a pitch that they substantially circle once on the inner peripheral surface 2' of the outer cylindrical portion 2. The grooves defined between the projecting ribs a,b are formed so that they have a constant width and their respective lower end portions generally extends to an upper surface 5 of a bottom wall between the outer cylindrical portion 2 and the inner cylindrical portion 3. Further, the angles formed between the projecting ribs a,b and a horizontal plane are acute. By the way, the term "the thickness ($t_1$) of the bottom wall" (see FIG. 2) as used herein means a distance between the plane 4 of truncation of the conical-frustum-shaped free end portion and the upper surface 5 of the bottom wall.

Incidentally, the height (H) of the inner cylindrical portion 3 from the upper surface 5 (reference plane) of the bottom wall between the outer and inner cylindrical portions (hereinafter called "both the cylindrical portions") 2,3, the inner diameter ($d_1$) of the outer cylindrical portion 2, the degree of tapering of an outer surface of the inner cylindrical portion 3, the difference ($\Delta H$) between both the cylindrical portions, and the like have been specified by the ISO (International Organization for Standardization). Data of the respective portions in the conventional art are, for example, as follows: thickness ($t_1$) of the bottom wall: about 1 mm or so, H: 9.20 mm, $\Delta H$: 2.1 mm, the degree of tapering: 6/100, and $d_1$: 7.80 mm.

Since the Luer-Lok portion 1 of the syringe according to the above-described conventional art is constructed as described above, excessive screwing of the connector 8 for the extension tube or the like in the Luer-Lok portion 1 in an attempt to make a free end portion of the connector 8 extend to the upper surface 5 of the bottom wall of the Luer-Lok portion 1 for the achievement of complete connection of the connector 8 upon connecting the connector 8 to the Luer-Lok portion 1 tends to cause bending of the free end portion of the connector 8 as shown in FIG. 4B so that the outer cylindrical portion 2 is pushed outwards. As a result, a stress is concentrated at a root portion of the outer cylindrical portion 2, leading frequently to breakage of the outer cylindrical portion 2 around the root portion. Through the root portion, the outer cylindrical portion is connected to the plane 4 of truncation of the conical-frustum-shaped free end portion. With a view to avoiding such breakage, various attempts have been made including making the thickness of a boundary area between a lower end portion of the outer cylindrical portion 2 of the Luer-Lok portion 1 and the plane 4 of truncation of the conical-frustum-shaped free end portion greater than that in the conventional art. Such attempts are however still insufficient to protect the Luer-Lok portion 1 from breakage. There is accordingly a desire for improvements.

SUMMARY OF THE INVENTION

An object of this invention is therefore to provide a syringe with a Luer-Lok portion, which is protected from breakage even when a connector for an extension tube, a three-way cock, a disposable needle or the like is excessively screwed in the Luer-Lok portion upon connecting the connector to the Luer-Lok portion.

The present inventors have proceeded with an extensive investigation to solve the above-described problem of the conventional art. As a result, it has been found that the problem that excessive screwing of the connector may cause bending of the free end portion of the connector as shown in FIG. 4B and the resulting concentration of a stress at the root portion of the outer cylindrical portion, through which root portion the outer cylindrical portion is connected to the plane of truncation of the conical-frustum-shaped free end portion, and the outer cylindrical portion is broken around the root portion thereof can be eliminated by (i) forming the lower end portion of at least one of the projecting ribs on the inner surface of the outer cylindrical portion at a position higher than the upper surface of the bottom wall between both the cylindrical portions although the lower end portions of the projecting ribs extend to the upper surface of the bottom wall in the conventional art, (ii) providing the at least one projecting rib with a stopper at a position upwardly apart a little from the lower end portion, or (iii) making the thickness of the root area of the outer cylindrical portion greater than that in the conventional art and further forming in the upper surface of the bottom wall an annular groove to be inserted with the free end portion of the connector and inserting the free end portion of the connector in the groove. Based on the above finding, the present inventors have succeeded in completing the present invention.

In a first aspect of the present invention, there is thus provided a syringe with a Luer-Lok portion for connecting an extension tube or the like, said Luer-Lok portion being arranged upright on a plane of truncation of a conical-frustum-shaped free end portion of the syringe and including an inner cylindrical portion and an outer cylindrical portion surrounding the inner cylindrical portion and having at least two projecting helical ribs formed in parallel with each other on an inner peripheral surface thereof, whereby the extension tube or the like can be connected to the Luer-Lok portion by screwing at least two projecting helical ribs of a cylindrical connector, said at least two projecting helical ribs being formed in parallel with each other on an outer peripheral surface of the cylindrical connector, in corresponding grooves defined between the helical projecting ribs of the outer cylindrical portion, wherein a lower end portion of at least one of the projecting helical ribs of the Luer-Lok portion is formed at a position higher than an upper surface of a bottom wall between both of the cylindrical portions.

In a second aspect of the present invention, there is also provided a syringe with a Luer-Lok portion for connecting an extension tube or the like, said Luer-Lok portion being arranged upright on a plane of truncation of a conical-frustum-shaped free end portion of the syringe and including an inner cylindrical portion and an outer cylindrical portion surrounding the inner cylindrical portion and having at least two projecting helical ribs formed in parallel with each other on an inner peripheral surface thereof, whereby the extension tube or the like can be connected to the Luer-Lok portion by screwing at least two projecting helical ribs of a cylindrical connector, said at least two projecting helical ribs being formed in parallel with each other on an outer peripheral surface of the cylindrical connector, in corresponding grooves defined between the helical projecting ribs of the outer cylindrical portion, wherein a lower end portion of at least one of the projecting helical ribs of the Luer-Lok portion extends to an upper surface of a bottom wall between both of the cylindrical portions, and the at least one projecting helical rib is provided with a stopper at a position upwardly apart from the lower end portion, whereby excessive screwing of the connector in the Luer-Lok portion can be prevented.

In a third aspect of the present invention, there is also provided a syringe with a Luer-Lok portion for connecting an extension tube or the like, said Luer-Lok portion being arranged upright on a plane of truncation of a conical-frustum-shaped free end portion of the syringe and including an inner cylindrical portion and an outer cylindrical portion surrounding the inner cylindrical portion and having at least two projecting helical ribs formed in parallel with each other on an inner peripheral surface thereof, whereby the extension tube or the like can be connected to the Luer-Lok portion by screwing at least two projecting helical ribs of a cylindrical connector, said at least two projecting helical ribs being formed in parallel with each other on an outer peripheral surface of the cylindrical connector, in corresponding grooves defined between the helical projecting ribs of the outer cylindrical portion, wherein a bottom wall between both of the cylindrical portions has a thickness greater than a conventional thickness, and an annular groove with a width and a depth sufficient to permit insertion of at least a part of a free end portion of the cylindrical connector is formed in an upper surface of the bottom wall.

The present invention can therefore provide a syringe with a Luer-Lok portion, in which the Luer-Lok portion is protected from breakage even when a connector for an extension tube, a three-way cock, a disposable needle or the like is excessively screwed in the Luer-Lok portion upon connecting the connector to the Luer-Lok portion.

DETAILED DESCRIPTION OF THE INVENTION AND PREFERRED EMBODIMENTS

The present invention will next be described in further detail on the basis of the drawings which illustrate the embodiments of the present invention and their modifications.

Figure 1A:
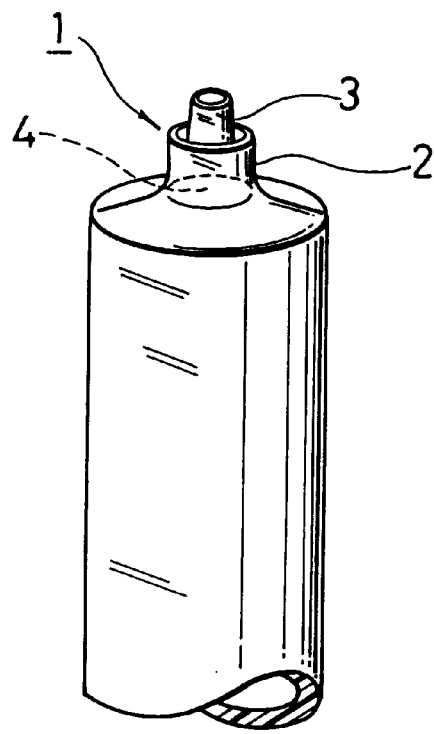
FIG. 1A is the perspective view of the conventional syringe having the Luer-Lok portion.
Figure 1B:
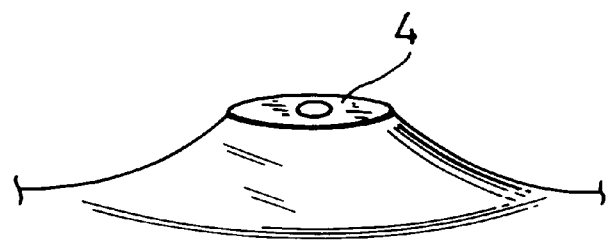
FIG. 1B is the enlarged perspective view of the conical-frustum-shaped free end portion of the conventional syringe without the Luer-Lok portion.
Figure 2:
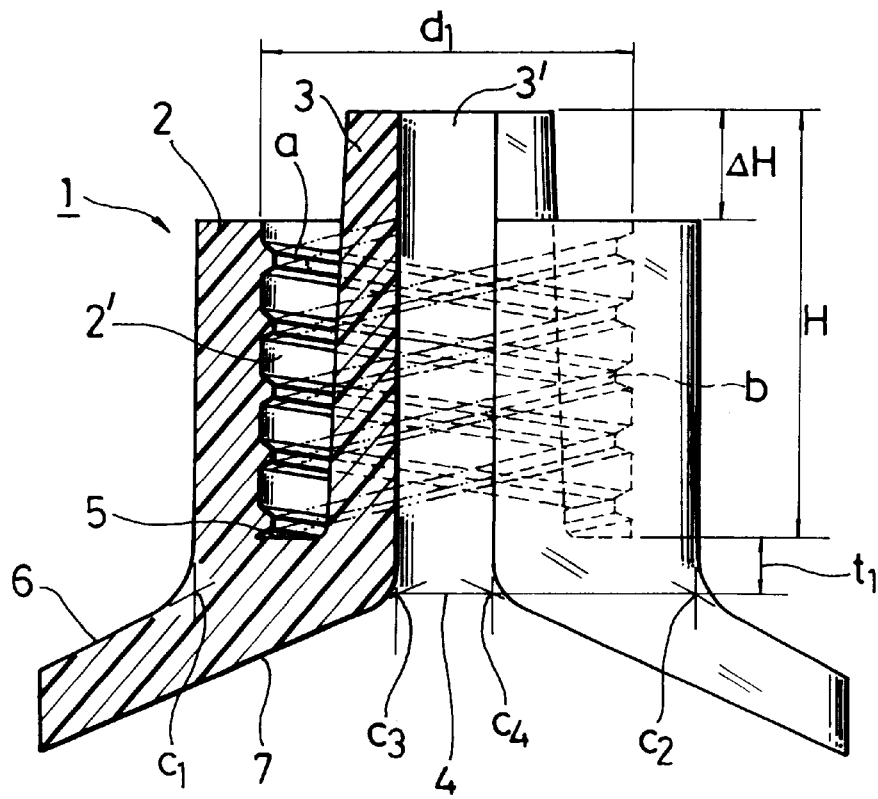
FIG. 2 is the schematic cross-sectional view of the Luer-Lok portion of the conventional syringe.

FIG. 1A is the perspective view of the syringe having the general Luer-Lok portion 1 according to the conventional art, in which only a part of a syringe main body is shown. Further, FIG. 2 is the schematic cross-sectional view of the conventional Luer-Lok portion 1 of the syringe. The Luer-Lok portion 1 is integrally formed on the plane 4 of truncation of the conical-frustum-shaped free end portion of the syringe.

The plane 4 of truncation lies in an imaginary plane containing a line which extends through intersecting points ($c_1, c_2$) between a lower extremity of an outer peripheral surface of the outer cylindrical portion 2 and an outer surface 6 of the conical-frustum-shaped free end portion of the syringe and intersecting points ($c_3, c_4$) between a lower extremity of an inner surface 3' of the inner cylindrical portion 3 and an inner surface 7 (i.e., the surface located on a side where an injection or the like is to be filled) of the conical-frustum-shaped free end portion of the syringe.

Figure 3:
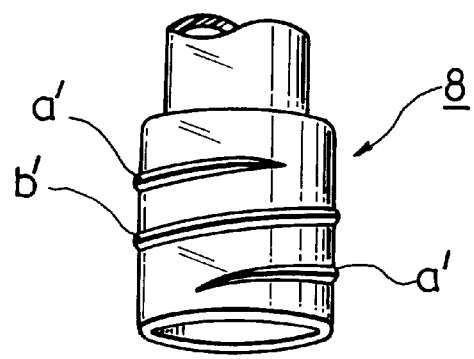
FIG. 3 is the perspective view of the cylindrical connector to be screwed in the Luer-Lok portion of the conventional syringe.

As is depicted in FIG. 2, the Luer-Lok portion 1 is composed of the outer cylindrical portion 2 and the inner cylindrical portion (Luer-Lok nozzle) 3, and the cylindrical connector 8 for the extension tube or the like, said connector being shown in perspective in FIG. 3, is screwed in a space between both of the cylindrical portions so that the cylindrical connector 8 and the Luer-Lok portion 1 are brought into engagement with each other. To assure the connection between the Luer-Lok portion 1 and the connector 8 at this time and also to prevent any detachment of the connector 8 from the Luer-Lok portion 1 during use, the outer cylindrical portion 2 and the connector 8 (see FIG. 3) are usually provided at their inner peripheral surface 2' and outer peripheral surface with the two projecting ribs a,b and the two projecting ribs a',b', respectively. The outer peripheral surface of the inner cylindrical portion 3 is formed at the same degree of tapering as the inner peripheral wall of the connector 8 to establish close contact fitting with the inner peripheral surface of the connector 8.

On the inner peripheral surface 2' of the outer cylindrical portion 2, the projecting ribs a,b are formed so that they helically extend downwards in parallel with each other. Upper end portions of these projecting ribs a,b are located, for example, in an upper part of the inner peripheral wall 2' of the outer cylindrical portion 2 with an angular interval of 180 degrees therebetween. The projecting ribs a,b have the same pitch, and in general, the projecting ribs a,b extend to the lower extremity of the inner peripheral surface 2' of the outer cylindrical portion 2 (i.e., the upper surface 5 of the bottom wall between both of the cylindrical portions) while making a circle from an upper part to a lower part on the inner peripheral surface 2' of the outer cylindrical portion 2. In the example shown in FIG. 2, however, the projecting ribs a,b extend to the upper surface 5 of the bottom wall while making two circles on the inner surface 2' of the outer cylindrical portion 2. Incidentally, actual projecting ribs are in the form of gentle curves although the projecting ribs a,b are shown in the form of straight lines in FIG. 2. As is illustrated in FIG. 2, the projecting ribs a,b have substantially the same width from their upper ends to their lower ends.

Figure 4A:
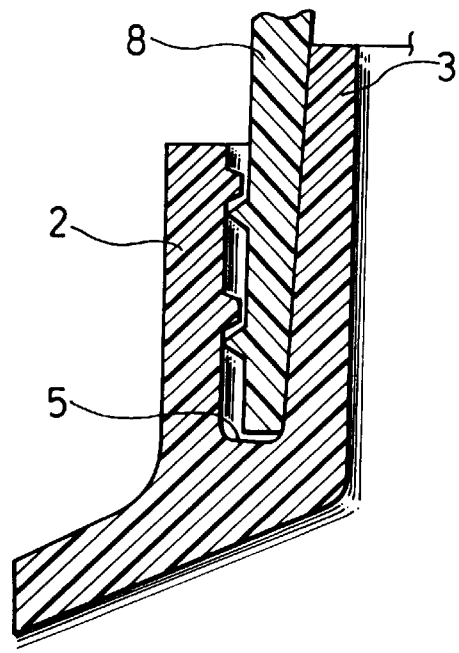
FIG. 4A is the simplified cross-sectional view illustrating the normal state of connection between the connector and the Luer-Lok portion.
Figure 4B:
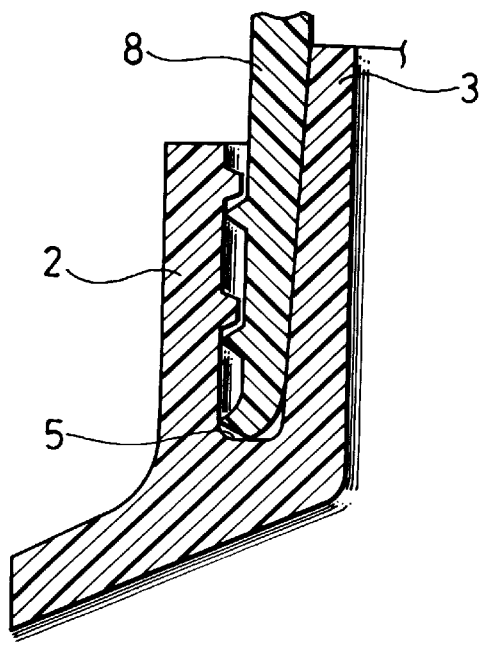
FIG. 4B is the simplified cross-sectional view depicting the state of connection between the connector and the Luer-Lok portion, in which the connector has been excessively screwed in the Luer-Lok portion.
Figure 5:
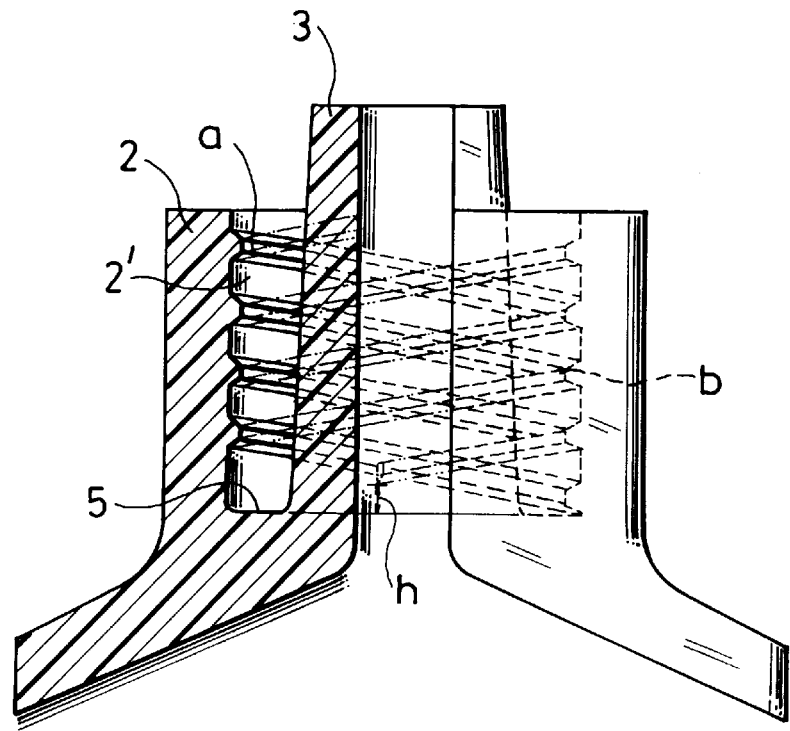
FIG. 5 is a schematic cross-sectional view of a Luer-Lok portion of a syringe according to an embodiment of the first aspect of the present invention.

Compared with the above-described syringe of the conventional art, the characteristic feature of the syringe according to the first aspect of the present invention resides in that, as one embodiment thereof is shown in schematic cross-section in FIG. 5, the lower end portion of at least one of at least two, usually two mutually-parallel projecting ribs a,b formed on the inner peripheral surface 2' of the outer cylindrical portion 2 of the Luer-Lok portion 1, preferably the lower end portions of all the projecting ribs are each formed at a position higher than the upper surface 5 of the bottom wall between both of the cylindrical portions. This construction has made it possible to protect the root area of the outer cylindrical portion 2 of the Luer-Lok portion 1 even when the cylindrical connector 8 for the extension tube or the like is excessively screwed in the Luer-Lok portion 1 upon bringing the connector 8 into engagement with the Luer-Lok portion 1. Described specifically, even when the lower end portion of the projecting rib a' of the connector 8 shown in FIG. 3 is screwed in beyond the lower end portion of the projecting rib a formed on the inner peripheral surface 2' of the outer cylindrical portion 2 depicted in FIG. 5, the lower end portion of the projecting rib a' is allowed to bend upwardly because the projecting rib a does not exists there. As a consequence, the force which outwardly pushes the outer cylindrical portion 2 is smaller compared with the outward force in the situation of the conventional art as shown in FIG. 4B. Accordingly, it is possible to avoid concentration of a stress around the root area of the outer cylindrical portion 2 and to protect the root area from breakage.

No particular limitation is imposed on the height (h) of the lower end portion of the projecting rib a from the upper surface 5 of the bottom wall (see FIGS. 5 and 6), insofar as sure connection of the connector 8 to the Luer-Lok portion 1 is feasible, the connection between the Luer-Lok portion 1 and the connector 8 does not become loose during use, and the screwed insertion of the connector 8 is stopped before the lower end portion of the connector 8 is brought into contact with the upper surface 5 of the bottom wall. The distance between the upper surface 5 of the bottom wall and the lower end portion of the connector 8 may preferably be at least 0.2 mm, with 0.3 to 2 mm being more preferred and 0.5 to 1.5 mm being particularly preferred.

Figure 7:
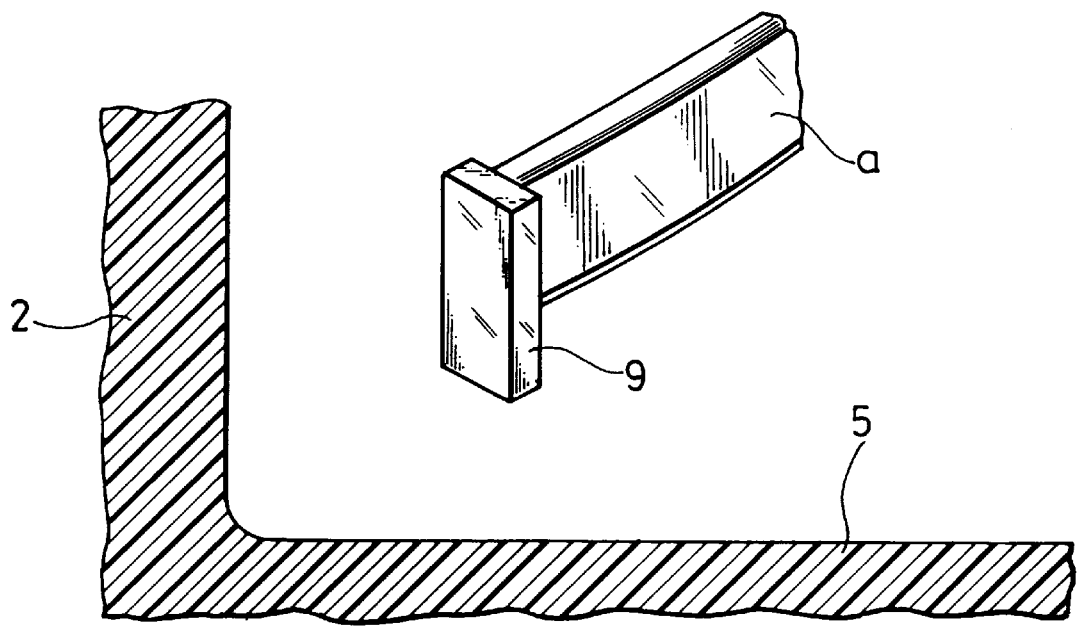
FIG. 7 is an enlarged schematic perspective view of a lower end portion of a projecting rib in a Luer-Lok portion of a syringe according to a modification of the embodiment of the second aspect of the present invention.

In the present invention, the protection of the outer cylindrical portion 2 of the Luer-Lok portion 1 from breakage even when the connector 8 is screwed in under large force can be ensured by arranging a stopper at the lower end portion of the projecting rib a in addition to the formation of the lower end portion of the projecting rib a at the above-described height. No particular limitation is imposed on the shape of the stopper and the stopper can be formed in any shape, insofar as the stopper can prevent excessive screwed insertion of the connector 8. For a preferred shape of the stopper, reference may be had to FIG. 7 by way of example. Namely, the width of the projecting rib a is enlarged at a particular position in the vicinity of the lower end portion thereof to reduce the width of the associated inter-rib groove there. The enlarged portion of the projecting rib a therefore acts as a stopper 9 so that the projecting rib a' of the connector 8 cannot move downwardly beyond the enlarged portion.

Figure 6:
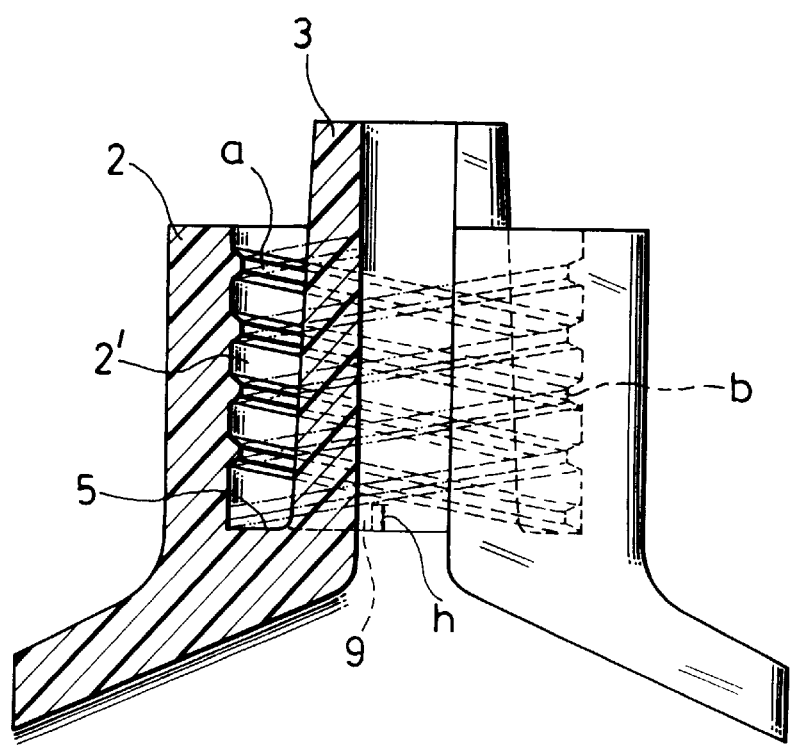
FIG. 6 is a schematic cross-sectional view of a Luer-Lok portion of a syringe according to an embodiment of the second aspect of the present invention.
Figure 8:
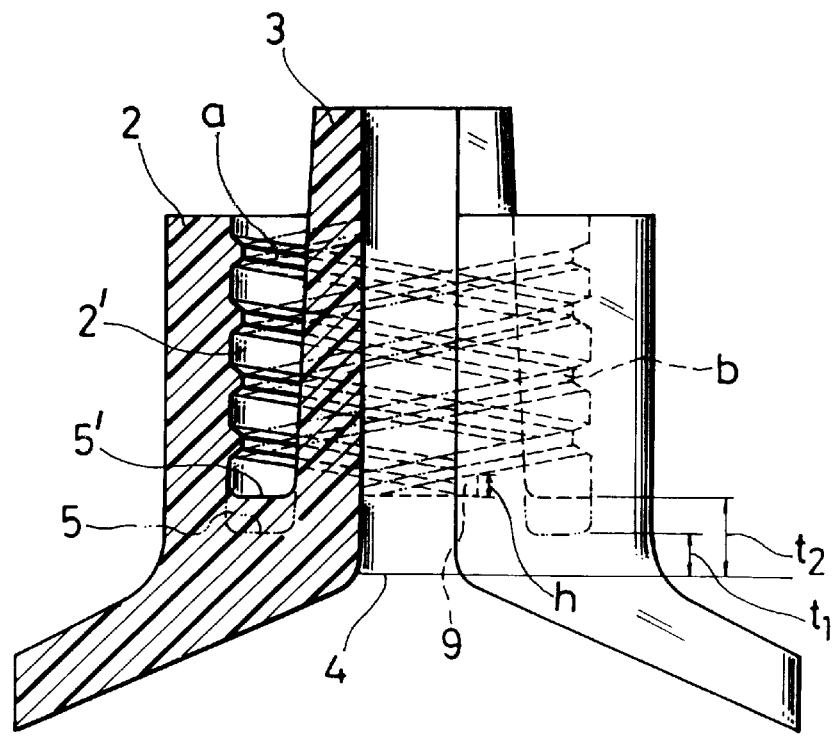
FIG. 8 is a schematic cross-sectional view of a Luer-Lok portion of a syringe according to a modification of the embodiment of the second aspect of the present invention.

As an alternative, reference may be had to FIGS. 6 and 8. As in the second aspect of the present invention, the projecting rib a is formed to extend to the upper surface 5 of the bottom wall in much the same way as in the conventional art, and the associated groove is filled up in a portion thereof located lower than the height (h) from the upper surface 5 of the bottom wall so that the free end portion of the projecting rib a' of the connector 8 is brought into abutment against the filled-up portion of the groove to prevent any further downward movement of the projecting rib a' of the connector 8. The filled-up portion of the groove acts as a stopper 9.

Concerning the stopper 9, the projecting rib a alone has been referred to. It is however preferred to also provide the projecting rib b with another stopper. In this case, the projecting rib b' of the connector 8 is brought into engagement with the another stopper. As to the filled-up portion of the groove, it is not absolutely necessary to fill up the groove in the entire portion thereof located lower than the height (h) from the upper surface 5 of the bottom wall. A lowermost portion of the groove may be left unfilled as far as the filled-up portion of the groove is provided with sufficient strength as a stopper.

A description will next be made about the third aspect of the present invention.

Figure 9:
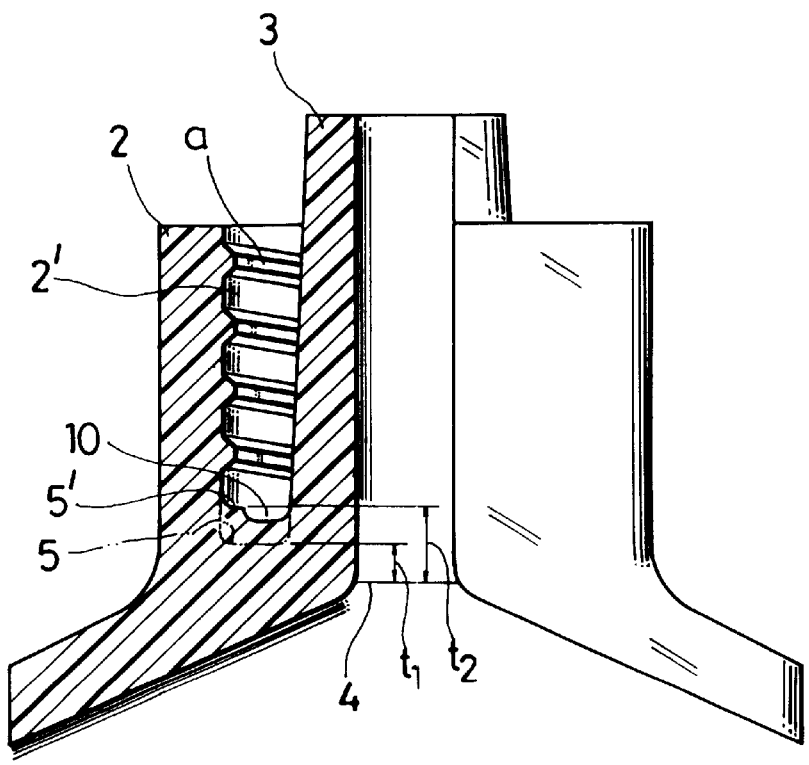
FIG. 9 is a schematic cross-sectional view of a Luer-Lok portion of a syringe according to an embodiment of the third aspect of the present invention.

The characteristic features of the third aspect of the present invention reside in that, as is illustrated by way of example in FIG. 9, the thickness ($t_2$) of a bottom wall between an outer cylindrical portion 2 and an inner cylindrical portion 3 is made greater than the thickness ($t_1$) in the conventional art and in contact with the outer peripheral surface of the inner cylindrical portion 3, an annular groove 10 is formed in an upper surface 5' of the bottom wall. The term "thickness" as used in the above description means the distance between the plane 4 of truncation of the conical-frustum-shaped free end portion of the syringe. The thickness $t_1$ is the thickness in the conventional art, while the thickness $t_2$ is the thickness in the third aspect of the present invention.

Figure 10:
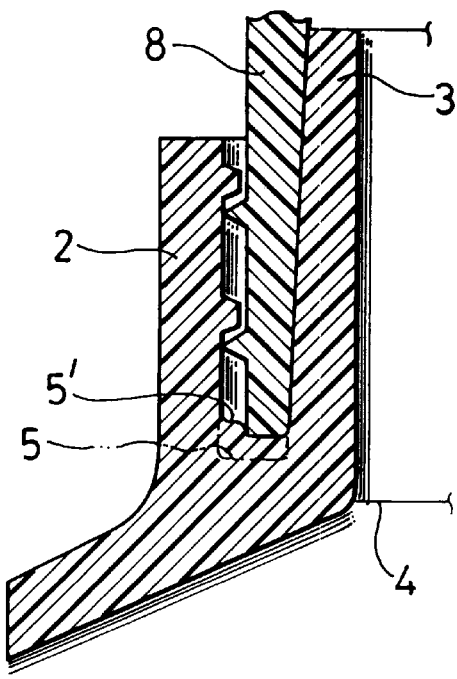
FIG. 10 is a schematic fragmentary cross-sectional view illustrating a state of connection of a connector with the Luer-Lok portion of the syringe according to the embodiment of the third aspect of the present invention.

The increase of the thickness of the bottom wall from $t_1$ to $t_2$ is to reinforce the root portion of the outer cylindrical portion 2. Further, the annular groove 10 serves, as illustrated in FIG. 10, to prevent the free end portion of the cylindrical connector 8 for the extension tube or the like from bending as shown in FIG. 4B and then pushing out the outer cylindrical portion 2 even if the cylindrical connector 8 is excessively screwed in.

Since the heights of the outer cylindrical portion 2 and the inner cylindrical portion 3 from the plane 4 of truncation of the conical-frustum-shaped free end portion of the syringe are standardized, the thickness ($t_2$) of the bottom wall should be in such a range that the heights of the outer cylindrical portion 2 and the inner cylindrical portion 3 from the plane 4 of truncation of the conical-frustum-shaped free end portion remain unchanged. An increase in the thickness of the bottom wall is in a range of from 2 to 35%, preferably from 5 to 20% compared with the corresponding thickness in the conventional art. Because the actual thickness ($t_1$) in the conventional art is about 1 mm, the thickness ($t_2$) of the bottom wall in the third aspect of the present invention may preferably be in a range of from 1.02 to 1.35 mm, with a range of from 1.05 to 1.2 mm being more preferred.

In other words, it is preferred to set the thickness ($t_2$) of the bottom wall in such a way that the height of the inner cylindrical portion 3 from the upper surface 5' of the bottom wall falls within a range of from 98 to 65% of the height of the inner cylindrical portion 3 in the conventional art. A thickness smaller than 98% cannot bring about sufficient reinforcing effect for the root portion of the outer cylindrical portion 2, whereas a thickness greater than 65% leads to unstable connection of the connector 8. A more preferred range is from 95 to 80%.

The annular groove 10 has a width and a depth sufficient to permit insertion of the free end portion of the cylindrical connector 8 for the extension tube or the like (see FIG. 3) and further to prevent at least a portion of the free end portion of the connector 8 from being disengaged from the groove 10 even when the connector 8 is excessively screwed in. No particular limitation is therefore imposed on these dimensions. Further, no particular limitation is imposed on the cross-sectional shape of the groove 10. A cross-sectional shape which permits easy insertion of the free end portion of the connector 8 into the groove 10 but prevents easy disengagement of the free end portion from the groove 10, such as a quadrilateral shape or a tapered shape upwardly flared on a side not in contact with the outer peripheral surface of the inner cylindrical portion 3, is preferred.

Formation of the Luer-Lok portion 1 as described above can reduce the concentration of a stress around the root of the outer cylindrical portion 2 of the Luer-Lok portion 1, which takes place when the cylindrical connector 8 for the extension tube or the like is excessively screwed in. This has made it possible to eliminate a problem such that the outer cylindrical portion 2 is broken up at the root thereof.

In the first aspect of the present invention, the thickness of the bottom wall between the outer cylindrical portion 2 and the inner cylindrical portion 3 can be increased thicker ($t_2$) than the thickness ($t_1$) in the conventional art for the purpose of reinforcement as described above as in the third aspect of the present invention if necessary (FIG. 8: the thickness is increased and the projecting ribs a,b extend to the upper surface 5' of the bottom wall between both of the cylindrical portions, and as in FIG. 6, the lower end portion of the groove is filled up to form the stopper 9). In this case, the value of $t_2$ is also similar to the corresponding value in the third aspect of the present invention.

In the present invention, no particular limitation is imposed on the cross-sectional shapes of the projecting ribs a,b on the inner peripheral wall 2' of the outer cylindrical portion 2, and the projecting ribs can be formed into a desired cross-sectional shape such as a circular, oval or quadrilateral cross-sectional shape. Further, the dimensions of the projecting ribs a,b can be set at preferred dimensions in view of the dimensions of the individual portions of the Luer-Lok portion 1, and no particular limitation is imposed thereon. In addition, no limitation is imposed on the pitch of the projecting ribs a,b.

The syringe with the Luer-Lok portion 1, which pertains to the present invention, is made of plastics. Any plastics can be used insofar as it can meet various properties required for syringes and various standard values for safety and sanitation, and no particular limitation is imposed thereon. Illustrative usable examples can include polyethylene, polypropylene, polystyrene, cyclic olefin resins, polycarbonates, polymethyl methacrylate, polyethylene terephthalate, and polybutylene terephthalate. Particularly preferred are cyclic olefin resins, including commercially available products such as "Zeonex" (trade mark, product of Nippon Zeon Co., Ltd.) and "Apel COC" (trade name, product of Mitsui Petrochemical Industries, Ltd.). Syringes according to the present invention can be manufactured by injection molding the above plastics in a manner known per se in the art.

A description will next be made of results of a confirmation of advantageous effects of the present invention.

Concerning each of the conventional syringe with the Luer-Lok portion 1 shown in FIG. 2 ($t_1$: 1.2 mm) and the invention syringes with the Luer-Lok portions illustrated in FIGS. 5, 6 and 9 (all of which had a capacity of 100 ml), twenty sample syringes were produced by injection molding while using a cyclic olefin resin ("Zeonex", trade mark; product of Nippon Zeon Co., Ltd.). In each sample syringe, a cylindrical connector 8 for an extension tube (manufactured by Kabushiki Kaisha Nemoto Kyorindo, the distance from the upper surface of the bottom wall to the lower end portion of each projecting rib: about 1 mm, the thickness of the free end portion: about 1 mm) was screwed in. A torque at which the outer cylindrical portion 2 was broken around its root portion was measured by using a torque meter ("2-TME45", trade name, manufactured by Kabushiki Kaisha Tohnich). The dimensions of each type of syringe samples and an average of torques measured on the twenty sample syringes of each type are shown in Table 1.

Incidentally, the number of projecting ribs formed on the inner peripheral wall 2' of the outer cylindrical portion 2 of the Luer-Lok portion 1 was 2, and each projecting rib had such a pitch that the projecting rib makes approximately a circle on the inner peripheral wall 2' of the outer cylindrical portion 2. The projecting ribs of the connector 8 and their pitch were similar.

TABLE 1

| Various dimensions | Comparative Example (FIG. 2) | Invention Example (FIG. 5) | Invention Example (FIG. 6) | Invention Example (FIG. 9) |
|---|---|---|---|---|
| Outer diameter of the upper end of the inner cylindrical portion (mm) | 3.948 | 3.948 | 3.948 | 3.948 |
| Outer cylindrical portion | | | | |
| Outer diameter (mm) | 9.80 | 10.00 | 10.00 | 10.00 |
| Inner diameter (mm) | 7.80 | 7.80 | 7.80 | 7.80 |
| Height of the inner cylindrical portion from the upper surface of the bottom wall between both of the cylindrical portion, H (mm) | 9.20 | 8.45 | 8.45 | 8.45 |
| Thickness increase of the bottom wall between both of the cylindrical portions, $t_2-t_1$ (mm) | 0 (standard) | 0 | 0 | 0.75 |
| Height of the lower end portion of each projecting helical rib from the upper surface of the bottom wall, h (mm) | 0 | 1.5 | 0 | 0 |
| Annular groove | | | | |
| Top width (mm) | No annular groove | No annular groove | No annular groove | 1.91 |
| Bottom width (mm) | | | | 1.51 |
| Depth (mm) | | | | 0.50 |
| Filling-up of groove (stopper) | Not filled | Not filled | Filled | Not filled |
| Average torque upon breakage of the outer cylindrical portion (kgf · cm) | 12.08 | 14.26 | 13.25 | 13.13 |

As is apparent from Table 1, the arrangement of the lower end portion of a projecting rib at a position higher than the upper surface of a bottom wall between both cylindrical portions, the arrangement of a stopper in association with a projecting rib, or the thickening of the bottom wall plus the formation of an annular groove in the upper surface of the bottom wall makes it possible to require a substantially higher torque for breaking an outer cylindrical portion than that required in the conventional art, thereby successfully protecting the outer cylindrical portion from breakage even when a connector is excessively screwed in.

What is claimed is:

1. A syringe comprising:
   a conical-frustum-shaped free end portion; and
   a Luer-Lok portion mounted on a plane of truncation of said conical-frustum-shaped free end portion and configured to attach at least one of an extension tube, a three-way cock and a disposable needle, said Luer-Lok portion including an inner cylindrical portion, an outer cylindrical portion surrounding said inner cylindrical portion, a bottom wall provided between said inner and outer cylindrical portions, said bottom wall including an upper surface, and at least two projecting helical ribs formed in parallel with each other on an inner peripheral surface of said outer cylindrical portion, said at least two projecting helical ribs defining grooves and at least one of said at least two projecting helical ribs including a lower end portion formed at a position higher than said upper surface of said bottom wall,
   wherein the at least one of an extension tube, a three-way cock and a disposable needle includes a cylindrical connector including at least two projecting helical ribs on an outer peripheral surface of said cylindrical connector, such that the at least one of an extension tube, a three-way cock and a disposable needle is attachable to said syringe by screwing said cylindrical connector into said Luer-Lok portion.

2. The syringe of claim 1, wherein said lower end portion of said at least one of said at least two projecting helical ribs on said inner peripheral surface of said outer cylindrical portion is formed 0.3 mm to 2.0 mm higher than said upper surface of said bottom wall.

3. The syringe of claim 1, wherein said end portion of said at least one of said at least two projecting helical ribs on said inner peripheral surface of said outer cylindrical portion is formed 0.5 mm to 1.5 mm higher than said upper surface of said bottom wall.

4. The syringe of claim 1, wherein said syringe comprises a cyclic olefin resin.

5. The syringe of claim 1, further comprising a stopper provided at said lower end portion of said at least one of said at least two projecting helical ribs.

6. The syringe of claim 1, wherein said bottom wall has a thickness in a longitudinal direction of said syringe greater than a thickness of a conventional bottom wall.

7. A syringe comprising:
   a conical-frustum-shaped free end portion; and
   a Luer-Lok portion mounted on a plane of truncation of said conical-frustum-shaped free end portion and configured to attach at least one of an extension tube, a three-way cock and a disposable needle, said Luer-Lok portion including an inner cylindrical portion, an outer cylindrical portion surrounding said inner cylindrical portion, a bottom wall between said inner and outer cylindrical portions, said bottom wall including an upper surface and having a thickness in a longitudinal direction of said syringe greater than a thickness of a conventional bottom wall, at least two helical ribs formed in parallel with each other on an inner peripheral surface of said outer cylindrical portion, said at least two projecting helical ribs defining grooves, and at least one annular groove formed in said upper surface of said bottom wall, wherein the at least one of an extension tube, a three-way cock and disposable needle includes a cylindrical connector including at least two projecting helical ribs on an outer peripheral surface of said cylindrical connector, such that the at least one of an extension tube, a three-way cock and a disposable needle is attachable to said syringe by screwing said cylindrical connector into said Luer-Lok portion.

8. The syringe of claim 7, wherein said thickness of said bottom wall is in a range between 1.02 and 1.35 mm.

9. The syringe of claim 7, wherein said thickness of said bottom wall is in a range between 1.05 and 1.2 mm.

10. The syringe of claim 7, wherein said thickness of said conventional bottom wall is 1 mm.

11. The syringe of claim 7, wherein said syringe comprises a cyclic olefin resin.

12. A syringe comprising:

a conical-frustum-shaped free end portion; and a Luer-Lok portion mounted on a plane of truncation of said conical-frustum-shaped free end portion and configured to attach at least one of an extension tube, a three-way cock and a disposable needle, said Luer-Lok portion including an inner cylindrical portion, an outer cylindrical portion surrounding said inner cylindrical portion, a bottom wall between said inner and outer cylindrical portions, said bottom wall including an upper surface, at least two projecting helical ribs formed in parallel with each other on an inner peripheral surface of said outer cylindrical portion, said at least two projecting helical ribs defining grooves and at least one of said at least two projecting helical ribs extending to said upper surface, and a stopper configured to stop said at least one of an extension tube, a three-way cock and a disposable needle from screwing excessively into said Luer-Lok portion, said stopper provided for said at least one of said at least two projecting helical ribs at a position upwardly apart from a lower end portion of said at least one of said at least two projecting helical ribs on said inner peripheral surface of said outer cylindrical portion, wherein the at least one of an extension tube, a three-way cock and a disposable needle includes a cylindrical connector including at least two projecting helical ribs on an outer peripheral surface of said cylindrical connector, such that the at least one of an extension tube, a three-way cock and a disposable needle is attachable to said syringe by screwing said cylindrical connector into said Luer-Lok portion.

13. The syringe of claim 12, wherein said stopper is formed by enlarging a width of said at least one of said at least two projecting ribs on said inner peripheral surface of said outer cylindrical portion at said position upwardly apart from said lower end portion.

14. The syringe of claim 12, wherein said stopper is formed by filling up a portion of one of said grooves defined by said at least two projecting helical ribs on said inner peripheral surface of said outer cylindrical portion, said portion of one of said grooves being formed on a lower side of said at least one of said at least two projecting ribs on said inner peripheral surface of said outer cylindrical portion, at said position upwardly apart from said lower end portion.

* * * * *